United States Patent
Shapiro

(10) Patent No.: US 7,560,422 B2
(45) Date of Patent: *Jul. 14, 2009

(54) ALCOHOL-BASED WIDE SPECTRUM DISINFECTANT COMPRISING NONOXYNOL-9

(75) Inventor: Allan Shapiro, Surrey (CA)

(73) Assignee: Alda Pharmaceuticals Corp., New Westminister, British Columbia (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/966,128

(22) Filed: Dec. 28, 2007

(65) Prior Publication Data

US 2008/0103210 A1    May 1, 2008

Related U.S. Application Data

(63) Continuation of application No. 10/525,110, filed as application No. PCT/CA02/01284 on Aug. 20, 2002, now Pat. No. 7,338,927.

(51) Int. Cl.
C11D 3/48 (2006.01)

(52) U.S. Cl. .................. 510/382; 510/131; 510/132; 510/157; 510/161; 510/199; 510/384; 510/356; 510/432

(58) Field of Classification Search .......... 510/382, 510/131, 132, 157, 161, 199, 384, 386, 432
See application file for complete search history.

(56) References Cited

U.S. PATENT DOCUMENTS

| | | | |
|---|---|---|---|
| 2,684,924 A | 7/1954 | Rose | |
| 2,990,425 A | 6/1961 | Senior | |
| 4,022,834 A | 5/1977 | Gundersen | |
| 4,420,484 A | 12/1983 | Gorman et al. | |
| RE32,300 E | 12/1986 | Gorman | |
| 4,766,113 A * | 8/1988 | West et al. | 514/187 |
| 4,870,108 A | 9/1989 | Page | |
| 5,017,617 A | 5/1991 | Kihara | |
| 5,030,659 A | 7/1991 | Bansemir | |
| 5,064,635 A * | 11/1991 | Casey | 510/100 |
| 5,284,875 A | 2/1994 | Martin | |
| 5,335,373 A * | 8/1994 | Dresdner et al. | 2/161.7 |
| 5,380,529 A | 1/1995 | Heusser et al. | |
| 5,387,611 A | 2/1995 | Rubinstein | |
| 5,591,442 A * | 1/1997 | Diehl et al. | 424/401 |
| 5,629,350 A | 5/1997 | Gartner | |
| 5,776,430 A | 7/1998 | Osborne | |
| 5,800,827 A | 9/1998 | Igarashi | |
| 5,902,593 A | 5/1999 | Kent | |
| 5,985,931 A | 11/1999 | Modak | |
| 6,121,327 A | 9/2000 | Tsuzuki | |
| 6,147,120 A | 11/2000 | Swart | |
| 6,153,568 A | 11/2000 | McCanna | |
| 6,187,327 B1 | 2/2001 | Stack | |
| 6,294,186 B1 | 9/2001 | Beerse | |
| 6,503,952 B2 | 1/2003 | Modak | |
| 7,338,927 B2 | 3/2008 | Shapiro | |
| 2002/0028229 A1 | 3/2002 | Lezdey | |
| 2002/0064544 A1 | 5/2002 | Lezdey | |
| 2003/0152644 A1 | 8/2003 | Modak | |
| 2004/0219227 A1 | 11/2004 | Modak | |
| 2004/0247685 A1* | 12/2004 | Modak et al. | 424/488 |

FOREIGN PATENT DOCUMENTS

| | | |
|---|---|---|
| CA | 1290250 | 10/1991 |
| CA | 1332136 | 9/1994 |
| CA | 1335352 | 4/1995 |
| CA | 2132688 | 3/1996 |
| CA | 2023287 | 1/1997 |
| CA | 2252555 | 12/1997 |
| CA | 2309353 | 5/1999 |
| CA | 2259780 | 7/1999 |
| CA | 2343325 | 3/2000 |
| CA | 2362601 | 6/2001 |
| DE | 2723303 | 11/1978 |
| EP | 0356264 | 2/1990 |
| FR | 2690457 | 10/1993 |

OTHER PUBLICATIONS

Evaluation of anti-microbial efficacy of a nonporous surface disinfectant Feb. 10, 1997.*
Anti-bacterial efficacy fo SPRITZ against various bacteria found in 27 drain pipe.
ALDA Pharmaceuticals Inc.—Infection Control At Its Best.
ALDA Pharmaceuticals Inc. Business Plan.
Executive Summary for ALDA Investor Presentations.
Key message points for ALDA Investor Presentations.

(Continued)

Primary Examiner—Charles I Boyer
(74) Attorney, Agent, or Firm—Porter, Wright, Morris & Arthur, LLP

(57) ABSTRACT

The invention discloses methods of making and uses for wide spectrum disinfectants including as components an alcohol, O-phenylphenol, chlorhexidine gluconate, nonoxynol-9, benzalkonium chloride, and deionized double distilled water wherein on a weight/volume ratio the alcohol comprises from 50% to 80%, the O-phenylphenol comprises from 0.1% to 0.8%, the chlorhexidine gluconate comprises from 0.1% to 1%, the nonoxynol-9 comprises from 0.02% to 1%, and the benzalkonium chloride comprises from 0.15% to 1%.

99 Claims, No Drawings

OTHER PUBLICATIONS

Table comparing properties of VIRALEX to Envirocide.
VIRALEX with $T^36$.
Product Description.
Pertinent Facts Regarding SPRITZ.
SPRITZ Dilution Properties.
SPRITZ—A Wide Spectrum Hard Surface Disinfectant—Designed for the Millenium.
SPRITZ—Wide Spectrum Hard Surface Disinfection.
Material Safety Data Sheet.
WHMIS Product Classification Summary.
Infection Control Guide.
Paramedic Academy Learning Center.
Protocol for Management of Exposure to Infectious Agents for Emergency.
Acute Oral Toxicity Study in Rats—Limit Test.
Primary Skin Irritation Study in Rabbits.
Primary Eye Irritation Study in Rabbits.
Acute Inhalation Toxicity Study in Rats—Limit Test.
Acute Dermal Toxicity Study in Rats—Limit Test.
Dermal Sensitization Study in Guinea Pigs (Buehler Method).
Germicidal Spray Products.
Virucidal Efficacy of a Disinfectant for Use on Inanimate Environmental Surfaces.
Fungicidal Germicidal Spray Products.
Evaluation of Anti-Microbial Efficacy of a Nonporous Surface Disinfectant.
Final Research Report.
Office Action dated Jul. 27, 2006 for U.S. Appl. No. 10/525,110.
Martindale: The Extra Pharmacopoeia, 28th Ed. (1982), The Pharmaceutical Press (London), pp. 373-374.
Gerald McDonnell and Denver Russell, Anticeptics and Disinfectants: Activity, Action, and Resistance, Clinical Microbology Reviews (Jan. 1999) vol. 12, No. 1, pp. 147-179.

* cited by examiner

ALCOHOL-BASED WIDE SPECTRUM DISINFECTANT COMPRISING NONOXYNOL-9

CROSS-REFERENCE TO RELATED APPLICATIONS

This application is a continuation application of U.S. patent application Ser. No. 10/525,110 filed on Feb. 18, 2005 now U.S. Pat. 7,338,927 which is the U.S. national stage of International Application Number PCT/CA2002/001284 filed on Aug. 20, 2002, the disclosures of which are expressly incorporated herein in their entireties by reference.

FIELD OF THE INVENTION

The invention relates generally to the field of disinfectants and in particular to wide spectrum disinfectants.

BACKGROUND OF THE INVENTION

It is known in that art that there are many compounds which can act as a disinfecting agent. For example, solutions of 70-85% (volume/volume) ethanol are commonly used as disinfectants. As is known in the art, there are two forms of ethanol generally available in North America: denatured ethanol, and potable alcohol. Both denatured and potable ethanols are used in the preparation of the solutions noted above. Denatured ethanol contains additives for the purpose of preventing or reducing abuse or consumption of the alcohol. Such additives may include aviation fuel, emetics, various organic solvents and mercury salts. Bitrex® (denatonium benzoate) is an example of an additive that is commonly present in ethanol in varying amounts. For instance, Bitrex® (denatonium benzoate) is present in specially denatured alcohol grade-3 (SDAG-3) at 700 mg per 100 liters, and is present in specially denatured alcohol grade-6 (SDAG-6) at 1 g per 100 liters. Solutions of 70-85% ethanol are effective in inactivating most vegetative bacteria, fungi, and lipid containing viruses. However, ethanol is not effective against bacterial spores.

As noted above, disinfecting agents vary in their ability to kill different microorganisms. For example, some compounds may act as a bactericide only, other as a virucide only, and yet others as a fungicide only. Some compounds are known which may kill gram-positive bacteria, yet not be effective in killing gram-negative bacteria. Accordingly, a disinfectant that can effectively kill most if not all microorganisms may require a combination of known disinfecting agents with complementary activity in order to provide a wide spectrum disinfectant.

Combinations of disinfecting agents can compound the risks associated with the use of any of those agents individually. Due to interactions between disinfecting agents, the combination may introduce new hazards in use, such as reduced efficacy of the disinfecting agents, irritation to the user, environmental risks such as flammability, and reduced residual effects of the disinfecting agents.

U.S. Reissue Pat. No. 32,300 describes the use of anti-microbial agents in combination with polyethylene glycol as a skin cleansing composition. The polyethylene glycol is used as a sudsing agent and lacks any anti-microbial properties. The anti-microbial agents suggested in that reissue patent have limited efficacy. In particular the combination described lacks tuberculocidal activity and has limited anti-viral activity. Further, the anti-microbial agents described in that reissue patent lose anti-microbial activity unless they are maintained in a non-ionic environment.

Canadian Patent No. 1,290,250 relates to an antiseptic fluid which, upon drying forms a skin protective film with residual anti-bacterial properties. The residual activity of the fluid described is dependent on a disposable film forming a polymer carrying specified bactericides. Due to its limited spectral efficiency the film is limited in the scope of its application and is not suitable for use in high infection risk environments.

Canadian Patent No. 1,332,136 describes the use of relatively high concentrations of a chlorhexidine salt complexed with a non-ionic surfactant in order to maintain a bactericidal activity, particularly against *Staphylococcus aureus*. However, chlorhexidine salts, such as chlorhexidine gluconate, in the relatively high concentrations described in Canadian Patent No. 1,332,136 irreversibly stains.

U.S. Pat. No. 5,030,659 describes an aqueous disinfectant using a combination of microbicidal compounds in specified ratios to broaden the spectrum of the anti-microbial activity. However, that disinfectant uses relatively high relative concentrations of benzalkonium chloride. The disinfectant described also lacks a denaturant or a cleanser resulting in a loss of potential disinfecting capacity. Further, at some concentrations of ethanol proposed in this patent, the disinfectant described is also combustible.

Canadian Patent No. 1,335,352 describes an oral bactericidal solution intended to prevent or inhibit growth of bacteria on tooth surfaces. The solution described includes at least one polymer which has one or more pendant polyalkylene oxide groups. It is stated that this solution enhances the anti-adhesive and antibacterial properties of tooth surfaces with a reduced risk of staining with chlorhexidine. However, it is not suggested that the solution has a broad spectrum of activity, or that it can act as a virucide or fungicide. Accordingly, the solution may be limited in its application to tooth surfaces.

U.S. Pat. No. 5,985,931 describes the use of a combination of antimicrobial agents in an aqueous solution to achieve a synergistic effect of the component anti-microbial agents. This solution suffers from a numbers of limitations. First, since the solution is about 70% water it will have some corrosive properties. Second, and notwithstanding any synergistic effects, the spectrum of organisms which the component anti-microbial agents can kill is not suggested to be broader. Accordingly, the solution will not be suitable for many uses required in a hospital grade product as it will not significantly reduce or kill *Mycobacterium tuberculosis*, and is of only limited utility in killing gram-negative bacteria and fungi.

Canadian Patent Application No. 2,132,688 describes a formulation that can act as a spermicide and virucide using a combination of benzalkonium chloride and nonoxynol. The purpose of the described formulation is as a vaginal application to protect against transmission of sexually transmitted viruses and other infections and to protect against conception. There is no suggestion in the description that this formulation has a broad spectrum of activity as a fungicide or bactericide. Further, there are some health concerns regarding the use of relatively high concentrations of nonoxynol and the possibility that nonoxynol when applied vaginally, may cause vaginal ulcerations.

Canadian Patent Application No. 2,309,353 describes an aqueous solution containing up to 20% by weight of a surfactant, and an anti-microbial quaternary ammonium compound. The anti-microbial activity of this solution is limited by the efficacy of the quaternary ammonium compound sued. In addition, the high aqueous level can render the product corrosive and thus limit its use to skin, nail, mouth and mucous membrane applications.

U.S. Pat. No. 4,870,108 describes a liquid antiseptic containing ethanol, acetone, glycerin, water, and a quaternary ammonium compound. This antiseptic is said to be rapid acting and non-irritating to skin after repeated use. However, there are problems with the use of the components of this liquid. Glycerin in the antiseptic prohibits the use of the solution on hard surfaces, instruments, and in high-risk areas. This antiseptic has limited residual anti-microbial activity, and for example, is not tuberculocidal. Further, the combination of acetone with ethanol is extremely flammable, and thus may present a safety risk in use.

Canadian Patent No. 2,023,287 describes the use of a combination of alcohols including benzyl alcohol to provide a broad spectrum antimicrobial composition. The specific combination of alcohols is said to have a lowered flash point when compared to previously available mixtures while providing synergistic effects on antimicrobial activity. However, the formulation suffers from the disadvantage that it is quite toxic and is not suitable for hospital grade disinfection. Further, the combination described is also water and moisture sensitive.

U.S. Pat. No. 5,800,827 describes compositions using an organic acid, with chlorhexidine in ethanol in concentrations greater than 50% by weight. The organic acid is believed to stabilize the chlorhexidine in the ethanol while maintaining the germicidal activity of the chlorhexidine. The organic acids described to stabilize the chlorhexidine are lactic acid and citric acid. However, while the chlorhexidine is stabilized, its spectrum of activity is unchanged. Thus, the compositions described are limited to the spectrum of activity of the chlorhexidine.

SUMMARY OF THE INVENTION

It is now an object of the present invention to provide a wide spectrum disinfectant wherein the disinfectant kills microorganisms quickly, and yet is safe for the user and is not environmentally harmful.

Accordingly the invention provides a wide spectrum disinfectant comprising SDAG-3 ethanol (95%), Bitrex® (denatonium benzoate), O-phenylphenol, benzalkonium chloride, chlorhexidine gluconate, nonoxynol-9, and deionized, double distilled water. The disinfectant can also optionally include a fragrance.

The invention further provides a process of manufacture of a wide spectrum disinfectant including the step of slowly bleeding deionized, double distilled water into an ethanol solution to avoid points of nucleation in the ethanol.

The invention further provides for the use of the disinfectant in medical and cosmetic applications.

The invention provides an environmentally friendly wide spectrum disinfectant, a method of manufacture of that disinfectant, and use of the disinfectant in medical and cosmetic applications.

In accordance with one aspect of the invention, there is provided wide spectrum disinfectant including as components an alcohol, O-phenylphenol, chlorhexidine gluconate, nonoxynol-9, benzalkonium chloride, and deionized double distilled water wherein on a weight/volume ratio the alcohol comprises from 50 to 80%, the O-phenylphenol comprises from 0.1 to 0.8%, the chlorhexidine gluconate comprises from 0.01 to 1%, the nonoxynol-9 comprises from 0.02 to 1%, and the benzalkonium chloride comprises from 0.15 to 1%.

In accordance with one embodiment of the invention, there is provided a wide spectrum disinfectant wherein the alcohol is selected from the group consisting of methanol, ethanol, propanol and butanol. In accordance with another embodiment of the invention, there is provided a wide spectrum disinfectant, wherein on a weight/volume ratio the alcohol comprises from 60 to 75%. In accordance with another embodiment of the invention, there is provided a wide spectrum disinfectant, wherein on a weight/volume ratio the alcohol comprises 70%. In accordance with another embodiment of the invention, there is provided a wide spectrum disinfectant, wherein on a weight/volume ratio the O-phenylphenol comprises from 0.2 to 0.5%. In accordance with another embodiment of the invention, wherein on a weight/volume ratio the nonoxynol-9 comprises from 0.04 to 0.1%.

In accordance with another aspect of the invention, there is provided a method of making the wide spectrum disinfectant of the invention including the steps of dissolving in alcohol at least one antimicrobial agent and continuing to stir the solution; dissolving in deionized, double distilled water at least a second antimicrobial agent; adding to the alcohol solution while continuing to stir, a detergent; adding to the alcohol solution while continuing to stir, the deionized, double distilled water solution at a sufficiently slow rate to prevent points of nucleation.

In accordance with another aspect of the invention, there is provided a method of making the wide spectrum disinfectant of the invention including the steps of dissolving in alcohol O-phenylphenol and continuing to stir the solution; dissolving in deionized, double distilled water benzalkonium chloride; adding to the alcohol solution while continuing to stir, nonoxynol-9 and chlorhexidine gluconate; adding to the alcohol solution while continuing to stir, the deionized, double distilled water solution at a sufficiently slow rate to prevent points of nucleation.

In accordance with another aspect of the invention, there is provided a method of making a wide spectrum disinfectant of the invention including the steps of dissolving in alcohol containing a denaturant O-phenylphenol and continuing to stir the solution; dissolving in deionized, double distilled water benzalkonium chloride; adding to the alcohol solution while continuing to stir, nonoxynol-9 and chlorhexidine gluconate; adding to the alcohol solution while continuing to stir, the deionized, double distilled water solution at a sufficiently slow rate to prevent points of nucleation.

In accordance with another aspect of the invention, there is provided a method of making a wide spectrum disinfectant of the invention including the steps of dissolving in alcohol containing a denaturant O-phenylphenol and continuing to stir the solution; dissolving in deionized, double distilled water benzalkonium chloride; adding to the alcohol solution while continuing to stir, nonoxynol-9, chlorhexidine gluconate and a fragrance; adding to the alcohol solution while continuing to stir, the deionized, double distilled water solution at a sufficiently slow rate to prevent points of nucleation.

DETAILED DESCRIPTION OF THE INVENTION

In one embodiment of the invention a fast acting disinfectant is described including the following (w/v): at least 50% alcohol; 0.1 to 0.8% O-phenylphenol; 0.01 to 1% chlorhexidine gluconate; 0.02 to 1% nonoxynol-9; 0.15 to 1% benzalkonium chloride; and deionized, double distilled water. One embodiment of the invention also includes Bitrex® (denatonium benzoate, as an emetic, fire-retardant denaturant) and a fragrance such as lemon fragrance no.431. The formulation for this embodiment is:

| Ingredient | Content (v/v) |
| --- | --- |
| SDAG-3 Ethanol 95% | 70.0% |
| Bitrex ® (denatonium benzoate) | 3.68% |
| O-phenylphenol | 0.28% |
| Benzalkonium chloride | 0.20% |
| Chlorhexidine gluconate | 0.01% |
| Nonoxynol-9 | 0.05% |
| Lemon fragrance No. 431 | 0.10% |
| Deionized/double distilled water | 25.68% |

The ability to kill mycobacterium is a key consideration in selecting a hospital grade product. The ability of formulations within the scope of the invention to kill mycobacterium have been tested using the following protocol. 55×13 mm diameter sterile coverslips were coated with approximately $10^5$ *Mycobacterium tuberculosis* strain Erdman ATCC#35801. This was achieved by adding $10^7$/ml of a suspension of mycobacteria at $10^7$/ml to the coverslip, spreading evenly with the tip of the applicator and allowing to air dry. A positive control group to assess the number of viable bacteria on the coverslip were processed by placing 5 coated coverslips into 500 ul broth, sonicated for 10 seconds with a probe sonicator to disperse the bacteria and serial dilutions plated onto agar growth media (Middlebrook 7H10). A negative control group was also prepared using 5 coverslips with no bacterial inoculation but otherwise processed as above. Test samples were prepared by coating coverslips by spraying the test disinfectant 3 times from a distance of 12 inches. The coverslips were then drained after either 1 minute or 5 minutes using Whatman filter paper and placed into 500 ul broth and processed as described above for the controls. Additional controls were also prepared using previously known disinfectants. These studies of the disinfectants effect on mycobacterium show that the above formulation falling within the scope of the invention has the highest $\log_{10} 6.54$ reduction scores presently known.

Residual mycobacterial disinfectant capacity was also tested by spraying test coverslips with the formulation forming the subject matter of the test three times from a distance of 12 inches and draining the coverslips as described above after either 1 minute or 5 minutes. One control group comprised coverslips which had not been inoculated with mycobacteria and a second control group comprised coverslips which while inoculated had not been treated with the test disinfectant formulation. The testing shows that embodiments of the invention have residual disinfecting activity suitable for rapidly killing mycobacterium.

Further, the formulation described is a powerful wide spectrum disinfectant. Spectrum studies confirm that the above formulation is 100% batericidal, fungicidal, virucidal, and tuberculocidal. Three minute exposure of various bacterial, fungal and viral cultures to disinfectants falling within the scope of the invention established the broad spectrum nature of these disinfectants including the ability to kill microorganisms including *Staphylococcus aureus* (ATCC 6538), *Salmonella cholerawsuis* (ATCC 10708), *Pseudomonas aeruginosa* (ATCC 15442), *Trichophyton mentagrophytes*, and Poliovirus type 1.

Further, tests to measure antiviral activity indicated the embodiments of the present invention were highly effective in preventing viral replication. Using a laboratory isolate of HIV-1 (HTLV-III$_B$, NIAID AIDS Reference Reagent Program, Rockville Md.) viral stocks were initially grown up to high titre in H9 lymphocytes suspended in RPMI viral culture medium supplemented with 10% fetal calf serum. After an appropriate number of passages, culture supernatants were harvested and stored at −70° C. in 1 mL aliquots for further use. Prior to the experiments being conducted, the viral stocks were titrated and diluted to yield $10^3$ infectious particles/culture. The diluted viral stocks were added to a pellet $2×10^6$ PHA-stimulated peripheral blood mononuclear cells that had been maintained in RPMI with 10% fetal calf serum, and supplemental penicillin, streptomycin, glutamine, rhIL-2 and PHA-P (1 ug/mL) for a period of three days. After incubation of the virus and the cell pellet for two hours at 37° C., the pellet was washed (to remove any adherent virus), then resuspended in fresh viral culture medium in the presence or absence of dilutions of the disinfectant formulation described above and the cultures were maintained to day 7. The supernatants were then harvested and stored at −70° C., for subsequent evaluation of p24 antigen levels (Organon Telcnika, Mississauga ON), as a measure of HIV replication in a given culture. The reduction in p24 antigen levels in the presence of a given dilution of the compound was taken as a measure of its antiretroviral activity. An uninfected culture and a positive control culture were included in the experiment. All experiments were conducted in triplicate, with the results presented as the mean of the three identical cultures. These studies showed that the embodiment of the present invention described above was 100% effective as a disinfectant on Human Immunodeficiency Virus (HIV) and related retroviruses upon contact.

As a further optional ingredient additional denaturants can also be added. These denaturants provide additional disinfecting properties since they denature genetic material, i.e. DNA and RNA. In denaturing the DNA and RNA, and having a broad spectrum of activity, disinfectants falling within the scope of the invention provide a more effective means of infection control than those previously known. In the preferred embodiment of the invention described above Bitrex® (denatonium benzoate) is used as a denaturant. However, Bitrex® (denatonium benzoate) also acts as an emetic to prevent or reduce the possibility of abuse of the solvent. Bitrex ® (denatonium benzoate) also acts as a fire retardant to prevent spontaneous combustion of the disinfectant.

The disinfectants of the present invention are also rapid acting in their disinfecting ability. Studies indicate that the embodiment of the invention described above provides maximal disinfection within 3 minutes.

In addition, toxicology studies confirm that the above formulation is both safe to the user and the environment. Toxicity studies were performed on the disinfectant formulation described above show, in accordance with Health Effects Test Guidelines:

| Test | Result | Protocol Used |
| --- | --- | --- |
| Acute Oral Toxicity | $LD_{50}$ > 5,000 mg/kg | OPPTS 870.1100 (1998) |
| Acute Dermal Toxicity | $LD_{50}$ > 2,000 mg/kg | OPPTS 870.1200 (1998) |
| Acute Inhalation Toxicity | $LC_{50}$ > 2.02 mg/L | OPPTS 870.1300 (1998) |
| Ocular Irritation | Average irritation score Unrinsed 29.0 Rinsed 27.3 | OPPTS 870.2400 (1998) |
| Dermal Irritation | PDII 0.0 | OPPTS 870.2500 (1998) |
| Dermal Sensitization | Not a contact sensitizer | OPPTS 870.2600 (1998) |

Finally, given the broad spectrum of activity of disinfectants falling within the scope of the invention, the existence of denaturants, the rapid action of the disinfectant, and their user and environmentally friendly nature the disinfectants of the present invention are particularly useful in medical situations such as hospitals and for paramedics.

The properties of the disinfectants of the present invention are desirable in a broad field of applications. They are suitable for use in the medical field, particularly where there is a high risk of contamination and infection. In addition to first responders such as ambulance, law enforcement and fire personnel, this invention can have application in the dental profession. Disinfectants of the present invention can also be used to prevent, or reduce the likelihood of transmission of sexually transmitted diseases. For example they can be used as components in a personal lubricant to reduce and prevent transmission of herpes, HIV and chlamydia.

In addition to being a powerful disinfectant, embodiments of this invention also act as a sanitizer, a cleanser and particularly where a fragrance is used in the formulation as a deodorizer. The detergent contained in the product (nonoxynol-9) is highly regarded as a powerful detergent, in addition to its anti-microbial properties. These additional properties of the invention make the formulations of this invention particularly attractive to the public health industry where disinfection is particularly important in public areas such as spas, hotels, restaurants, nursing homes and institutions such as penal institutions.

The invention has application to the beauty industry, particularly as an additive to some cosmetics. Some formulations of the invention be used as a percentage addition to creams and ointments as an anti-microbial component or as a component for single or multiple-use wipes.

The present invention also includes methods for making wide spectrum disinfectant formulations. In one embodiment, the method includes the steps of:

1. dissolving in ethanol at least one antimicrobial agent and continuing to stir the solution;
2. dissolving in deionized, double distilled water at least a second antimicrobial agent;
3. adding to the ethanol solution while continuing to stir, a detergent;
4. adding to the ethanol solution while continuing to stir, the deionized, double distilled water solution at a sufficiently slow rate to prevent points of nucleation.

The method of making disinfectants of the present invention can be more clearly illustrated using the specific example of the formulation described above. That formulation is manufactured by:

1. adding ethanol containing Bitrex® (denatonium benzoate) to a grounded mixing tank;
2. adding O-phenylphenol to the mixing tank containing ethanol slowly until the O-phenylphenol is fully dissolved. Once fully dissolved, continued mixing is preferred for an additional 15 minutes;
3. adding and continually mixing the fragrance, chlorhexidine gluconate and nonoxynol-9 to the grounded mixing tank;
4. bleeding double distilled deionized water into the mixing tank at a sufficiently slow rate to prevent shock to the solution in the tank and avoid points of nucleation.
5. adding and mixing benzalkonium chloride to the mixing tank, with continued mixing for an additional 30 minutes being preferred.

The mixture can then be filtered using a 0.20 micron filter and stored in sterilized bottles.

The sequence of addition of ingredients is important to the creation of the desired disinfectant. In the example described above, the OPP should be dissolved in the ethanol first. Other alcohols such can be used instead of ethanol, including methanol or 1-propanol. Further, the advantages of the present invention can also be realized using alcohol concentrations from about 50-80% (w/v). The addition of the OPP slowly to the ethanol ensures complete miscibility in solution. A complex compound is thus formed, allowing the OPP to remain a free radical, not bound to ethanol. Effectively the OPP dissolves in the ethanol to form a complex.

The nonoxynol-9, fragrance (if desired) and chlorhexidine gluconate are added before the addition of the water.

When manufacturing the disinfectant of the present invention care must be taken when adding the double distilled deionized water to the ethanol to avoid shocking the mixture in that the O-phenylphenol ("OPP") and possibly the added ingredients will separate from the solution, and precipitate, rendering the solution a failure.

Further, it is important that double distilled deionized water be used so as to avoid points of nucleation that would cause the O-phenylphenol to leave solution. Regular water will allow the OPP to leave the solution, ('points of nucleation'). OPP has a natural tendency to want to leave or form a guam thus separating from the alcohol when exposed to regular water. Additionally, the double distilled deionized water provides an environment whereby the micro-voltage and electrical field supports complete adhesion of the final disinfectant product to the targeted micro organism for proteolysis, cytolysis and ultimately cell death, as well as total destruction of the DNA and RNA.

The optional but desirable step of filtration of the disinfectant through a 0.20 micron filter ensures the disinfectant is free of any vegetative growth which could potentially compromise the quality and efficacy of the disinfectant. This step renders a final product free of any impurities. This step, coupled with the foil heat-induction seal of bottles for storage of the disinfectant creates a high quality, spore free, disinfectant.

Various embodiments of the present invention having been thus described in detail by way of example, it will be apparent to those skilled in the art that variations and modifications may be made without departing from the invention. The invention includes all such variations and modifications as fall within the scope of the appended claims.

What is claimed is:

1. A wide spectrum disinfectant prepared by a process comprising the steps of dissolving O-phenylphenol in alcohol with stirring to provide an alcohol solution; dissolving at least one antimicrobial agent in deionised, double distilled water to provide a deionised, double distilled water solution; adding a detergent to the alcohol solution while continuing to stir; and adding the deionised, double distilled water solution to the alcohol solution at a sufficiently slow rate to prevent points of nucleation and thereby prevent the O-phenylphenol from precipitating, wherein on a weight/volume ratio the alcohol comprises at least 50% of the wide spectrum disinfectant, and wherein said detergent is nonoxynol-9.

2. The wide spectrum disinfectant according to claim 1, wherein the alcohol is selected from the group consisting of methanol, ethanol, propanol and butanol.

3. The wide spectrum disinfectant according to claim 1, wherein the alcohol is ethanol.

4. The wide spectrum disinfectant according to claim 3, wherein the ethanol is a denatured ethanol.

5. The wide spectrum disinfectant according to claim 1, wherein on a weight/volume ratio the alcohol comprises from at least 50% to about 80%.

6. The wide spectrum disinfectant according to claim 1, wherein on a weight/volume ratio the alcohol comprises from about 60 to about 75%.

7. The wide spectrum disinfectant according to claim 1, wherein on a weight/volume ratio the O-phenylphenol comprises from about 0.1 to about 0.8%.

8. The wide spectrum disinfectant according to claim 1, wherein on a weight/volume ratio the O-phenylphenol comprises from about 0.2 to about 0.5%.

9. The wide spectrum disinfectant according to claim 1, wherein said at least one antimicrobial agent is benzalkonium chloride.

10. The wide spectrum disinfectant according to claim 9, wherein on a weight/volume ratio the benzalkonium chloride comprises from about 0.15 to about 1%.

11. The wide spectrum disinfectant according to claim 1, wherein said process further comprises adding an additional antimicrobial agent to said alcohol solution.

12. The wide spectrum disinfectant according to claim 11, wherein said additional antimicrobial agent is chlorhexidine gluconate.

13. The wide spectrum disinfectant according to claim 12, wherein on a weight/volume ratio the chlorhexidine gluconate comprises from about 0.01 to about 1%.

14. The wide spectrum disinfectant according to claim 1, wherein on a weight/volume ratio the nonoxynol-9 comprises from about 0.02 to about 1%.

15. The wide spectrum disinfectant according to claim 1, wherein on a weight/volume ratio the nonoxynol-9 comprises from about 0.04 to about 0.1%.

16. The wide spectrum disinfectant according to claim 1, wherein said process further comprises adding a denaturant to the alcohol solution.

17. The wide spectrum disinfectant according to claim 16, wherein the denaturant is Bitrex® (denatonium benzoate).

18. A method of preventing or reducing the transmission of a sexually transmitted disease, which comprises utilizing a wide spectrum disinfectant prepared by a process comprising the steps of dissolving O-phenylphenol in alcohol with stirring to provide an alcohol solution; dissolving at least one antimicrobial agent in deionised, double distilled water to provide a deionised, double distilled water solution; adding a detergent to the alcohol solution while continuing to stir; and adding the deionised, double distilled water solution to the alcohol solution at a sufficiently slow rate to prevent points of nucleation and thereby prevent the O-phenylphenol from precipitating, wherein on a weight/volume ratio the alcohol comprises at least 50% of the wide spectrum disinfectant and wherein said detergent is nonoxynol-9.

19. The method according to claim 18, wherein said sexually transmitted disease is herpes.

20. The method according to claim 18, wherein said sexually transmitted disease is chlamydia.

21. The method according to claim 18, wherein said sexually transmitted disease is human immunodeficiency virus (HIV) infection.

22. The method according to claim 18, wherein the wide spectrum disinfectant is a component of a personal lubricant.

23. The method according to claim 18, wherein the alcohol is selected from the group consisting of methanol, ethanol, propanol and butanol.

24. The method according to claim 18, wherein the alcohol is ethanol.

25. The method according to claim 24, wherein the ethanol is a denatured ethanol.

26. The method according to claim 18, wherein on a weight/volume ratio the alcohol comprises from at least 50% to about 80%.

27. The method according to claim 18, wherein on a weight/volume ratio the alcohol comprises from about 60 to about 75%.

28. The method according to claim 18, wherein on a weight/volume ratio the O-phenylphenol comprises from about 0.1 to about 0.8%.

29. The method according to claim 18, wherein on a weight/volume ratio the O-phenylphenol comprises from about 0.2 to about 0.5%.

30. The method according to claim 18, wherein said at least one antimicrobial agent is benzalkonium chloride.

31. The method according to claim 30, wherein on a weight/volume ratio the benzalkonium chloride comprises from about 0.15 to about 1%.

32. The method according to claim 18, wherein said process further comprises adding an additional antimicrobial agent to said alcohol solution.

33. The method according to claim 32, wherein said additional antimicrobial agent is chlorhexidine gluconate.

34. The method according to claim 33, wherein on a weight/volume ratio the chlorhexidine gluconate comprises from about 0.01 to about 1%.

35. The method according to claim 18, wherein on a weight/volume ratio the nonoxynol-9 comprises from about 0.02 to about 1%.

36. The method according to claim 18, wherein on a weight/volume ratio the nonoxynol-9 comprises from about 0.04 to about 0.1%.

37. The method according to claim 18, wherein said process further comprises adding a denaturant to the alcohol solution.

38. The method according to claim 37, wherein the denaturant is Bitrex® (denatonium benzoate).

39. The method according to claim 18, wherein said at least one antimicrobial agent is benzalkonium chloride, wherein said process further comprises adding an additional antimicrobial agent to said alcohol solution and said additional antimicrobial agent is chlorhexidine gluconate, and wherein on a weight/volume ratio the alcohol comprises from about 50 to about 80%, the O-phenylphenol comprises from about 0.1 to about 0.8%, the chlorhexidine gluconate comprises from about 0.01 to 1%, the nonoxynol-9 comprises from 0.02 to about 1%, and the benzalkonium chloride comprises from about 0.15 to 1%.

40. A method of reducing the risk of contamination and infection by bacteria, viruses and/or fungi which comprises utilizing a wide spectrum disinfectant prepared by a process comprising the steps of dissolving O-phenylphenol in alcohol with stirring to provide an alcohol solution; dissolving at least one antimicrobial agent in deionised, double distilled water to provide a deionised, double distilled water solution; adding a detergent to the alcohol solution while continuing to stir; and adding the deionised, double distilled water solution to the alcohol solution at a sufficiently slow rate to prevent points of nucleation and thereby prevent the O-phenylphenol from precipitating, wherein on a weight/volume ratio the alcohol comprises at least 50% of the wide spectrum disinfectant and wherein said detergent is nonoxynol-9.

41. The method according to claim 40, wherein said method is utilized in the medical field.

42. The method according to claim 40, wherein said method is utilized in the dental profession.

43. The method according to claim 40, wherein said method is utilized in the public health industry.

44. The method according to claim 40, wherein the alcohol is selected from the group consisting of methanol, ethanol, propanol and butanol.

45. The method according to claim 40, wherein the alcohol is ethanol.

46. The method according to claim 45, wherein the ethanol is a denatured ethanol.

47. The method according to claim 40, wherein on a weight/volume ratio the alcohol comprises from at least 50% to about 80%.

48. The method according to claim 40, wherein on a weight/volume ratio the alcohol comprises from about 60 to about 75%.

49. The method according to claim 40, wherein on a weight/volume ratio the O-phenylphenol comprises from about 0.1 to about 0.8%.

50. The method according to claim 40, wherein on a weight/volume ratio the O-phenylphenol comprises from about 0.2 to about 0.5%.

51. The method according to claim 40, wherein said at least one antimicrobial agent is benzalkonium chloride.

52. The method according to claim 51, wherein on a weight/volume ratio the benzalkonium chloride comprises from about 0.15 to about 1%.

53. The method according to claim 40, wherein said process further comprises adding an additional antimicrobial agent to said alcohol solution.

54. The method according to claim 53, wherein said additional antimicrobial agent is chlorhexidine gluconate.

55. The method according to claim 54, wherein on a weight/volume ratio the chlorhexidine gluconate comprises from about 0.01 to about 1%.

56. The method according to claim 40, wherein on a weight/volume ratio the nonoxynol-9 comprises from about 0.02 to about 1%.

57. The method according to claim 40, wherein on a weight/volume ratio the nonoxynol-9 comprises from about 0.04 to about 0.1%.

58. The method according to claim 40, wherein said process further comprises adding a denaturant to the alcohol solution.

59. The method according to claim 58, wherein the denaturant is Bitrex® (denatonium benzoate).

60. The method according to claim 40, wherein said at least one antimicrobial agent is benzalkonium chloride, wherein said process further comprises adding an additional antimicrobial agent to said alcohol solution and said additional antimicrobial agent is chlorhexidine gluconate, and wherein on a weight/volume ratio the alcohol comprises from about 50 to about 80%, the O-phenylphenol comprises from about 0.1 to about 0.8%, the chlorhexidine gluconate comprises from about 0.01 to 1%, the nonoxynol-9 comprises from 0.02 to about 1%, and the benzalkonium chloride comprises from about 0.15 to 1%.

61. A personal lubricant comprising a wide spectrum disinfectant prepared by a process comprising the steps of dissolving O-phenylphenol in alcohol with stirring to provide an alcohol solution; dissolving at least one antimicrobial agent in deionised, double distilled water to provide a deionised, double distilled water solution; adding a detergent to the alcohol solution while continuing to stir; and adding the deionised, double distilled water solution to the alcohol solution at a sufficiently slow rate to prevent points of nucleation and thereby prevent the O-phenylphenol from precipitating, wherein on a weight/volume ratio the alcohol comprises at least 50% of the wide spectrum disinfectant and wherein said detergent is nonoxynol-9.

62. The personal lubricant according to claim 61, wherein the alcohol is selected from the group consisting of methanol, ethanol, propanol and butanol.

63. The personal lubricant according to claim 61, wherein the alcohol is ethanol.

64. The personal lubricant according to claim 63, wherein the ethanol is a denatured ethanol.

65. The personal lubricant according to claim 61, wherein on a weight/volume ratio the alcohol comprises from at least 50% to about 80%.

66. The personal lubricant according to claim 61, wherein on a weight/volume ratio the alcohol comprises from about 60 to about 75%.

67. The personal lubricant according to claim 61, wherein on a weight/volume ratio the O-phenylphenol comprises from about 0.1 to about 0.8%.

68. The personal lubricant according to claim 61, wherein on a weight/volume ratio the O-phenylphenol comprises from about 0.2 to about 0.5%.

69. The personal lubricant according to claim 61, wherein said at least one antimicrobial agent is benzalkonium chloride.

70. The personal lubricant according to claim 69, wherein on a weight/volume ratio the benzalkonium chloride comprises from about 0.15 to about 1%.

71. The personal lubricant according to claim 61, wherein said process further comprises adding an additional antimicrobial agent to said alcohol solution.

72. The personal lubricant according to claim 71, wherein said additional antimicrobial agent is chlorhexidine gluconate.

73. The personal lubricant according to claim 72, wherein on a weight/volume ratio the chlorhexidine gluconate comprises from about 0.01 to about 1%.

74. The personal lubricant according to claim 61, wherein on a weight/volume ratio the nonoxynol-9 comprises from about 0.02 to about 1%.

75. The personal lubricant according to claim 61, wherein on a weight/volume ratio the nonoxynol-9 comprises from about 0.04 to about 0.1%.

76. The personal lubricant according to claim 61, wherein said process further comprises adding a denaturant to the alcohol solution.

77. The personal lubricant according to claim 76, wherein the denaturant is Bitrex® (denatonium benzoate).

78. The personal lubricant according to claim 61, wherein said at least one antimicrobial agent is benzalkonium chloride, wherein said process further comprises adding an additional antimicrobial agent to said alcohol solution and said additional antimicrobial agent is chlorhexidine gluconate, and wherein on a weight/volume ratio the alcohol comprises from about 50 to about 80%, the O-phenylphenol comprises from about 0.1 to about 0.8%, the chlorhexidine gluconate comprises from about 0.01 to 1%, the nonoxynol-9 comprises from 0.02 to about 1%, and the benzalkonium chloride comprises from about 0.15 to 1%.

79. A sanitizer or a cleanser comprising a wide spectrum disinfectant prepared by a process comprising the steps of dissolving O-phenylphenol in alcohol with stirring to provide an alcohol solution; dissolving at least one antimicrobial agent in deionised, double distilled water to provide a deionised, double distilled water solution; adding a detergent to the alcohol solution while continuing to stir; and adding the deionised, double distilled water solution to the alcohol solution at a sufficiently slow rate to prevent points of nucleation and thereby prevent the O-phenylphenol from precipitating, wherein on a weight/volume ratio the alcohol comprises at least 50% of the wide spectrum disinfectant and wherein said detergent is nonoxynol-9.

80. The sanitizer or the cleanser according to claim 79, wherein said sanitizer or cleanser is a component of a cream.

81. The sanitizer or the cleanser according to claim 79, wherein said sanitizer or cleanser is a component of an ointment.

82. The sanitizer or the cleanser according to claim 79, wherein said sanitizer or cleanser is a component of a single- or multiple-use wipe.

83. The sanitizer or the cleanser according to claim 79, wherein the alcohol is selected from the group consisting of methanol, ethanol, propanol and butanol.

84. The sanitizer or the cleanser according to claim 79, wherein the alcohol is ethanol.

85. The sanitizer or the cleanser according to claim 84, wherein the ethanol is a denatured ethanol.

86. The sanitizer or the cleanser according to claim 79, wherein on a weight/volume ratio the alcohol comprises from at least 50% to about 80%.

87. The sanitizer or the cleanser according to claim 79, wherein on a weight/volume ratio the alcohol comprises from about 60 to about 75%.

88. The sanitizer or the cleanser according to claim 79, wherein on a weight/volume ratio the O-phenylphenol comprises from about 0.1 to about 0.8%.

89. The sanitizer or the cleanser according to claim 79, wherein on a weight/volume ratio the O-phenylphenol comprises from about 0.2 to about 0.5%.

90. The sanitizer or the cleanser according to claim 79, wherein said at least one antimicrobial agent is benzalkonium chloride.

91. The sanitizer or the cleanser according to claim 90, wherein on a weight/volume ratio the benzalkonium chloride comprises from about 0.15 to about 1%.

92. The sanitizer or the cleanser according to claim 79, wherein said process further comprises adding an additional antimicrobial agent to said alcohol solution.

93. The sanitizer or the cleanser according to claim 92, wherein said additional antimicrobial agent is chlorhexidine gluconate.

94. The sanitizer or the cleanser according to claim 93, wherein on a weight/volume ratio the chlorhexidine gluconate comprises from about 0.01 to about 1%.

95. The sanitizer or the cleanser according to claim 79, wherein on a weight/volume ratio the nonoxynol-9 comprises from about 0.02 to about 1%.

96. The sanitizer or the cleanser according to claim 79, wherein on a weight/volume ratio the nonoxynol-9 comprises from about 0.04 to about 0.1%.

97. The sanitizer or the cleanser according to claim 79, wherein said process further comprises adding a denaturant to the alcohol solution.

98. The sanitizer or the cleanser according to claim 97, wherein the denaturant is Bitrex® (denatonium benzoate).

99. The sanitizer or the cleanser according to claim 79, wherein said at least one antimicrobial agent is benzalkonium chloride, wherein said process further comprises adding an additional antimicrobial agent to said alcohol solution and said additional antimicrobial agent is chlorhexidine gluconate, and wherein on a weight/volume ratio the alcohol comprises from about 50 to about 80%, the O-phenylphenol comprises from about 0.1 to about 0.8%, the chlorhexidine gluconate comprises from about 0.01 to 1%, the nonoxynol-9 comprises from 0.02 to about 1%, and the benzalkonium chloride comprises from about 0.15 to 1%.

* * * * *